(12) United States Patent
Bian

(10) Patent No.: US 11,408,909 B2
(45) Date of Patent: Aug. 9, 2022

(54) STEP COUNTING DEVICE AND METHOD

(71) Applicant: REALTEK SEMICONDUCTOR CORPORATION, Hsinchu (TW)

(72) Inventor: Ai-Hua Bian, Suzhou (CN)

(73) Assignee: REALTEK SEMICONDUCTOR CORPORATION, Hsinchu (TW)

( * ) Notice: Subject to any disclaimer, the term of this patent is extended or adjusted under 35 U.S.C. 154(b) by 102 days.

(21) Appl. No.: 17/117,160

(22) Filed: Dec. 10, 2020

(65) Prior Publication Data

US 2021/0181232 A1    Jun. 17, 2021

(30) Foreign Application Priority Data

Dec. 11, 2019 (CN) .......................... 201911277547.5

(51) Int. Cl.
*G01P 13/00* (2006.01)
*A63B 24/00* (2006.01)

(52) U.S. Cl.
CPC .......... *G01P 13/00* (2013.01); *A63B 24/0062* (2013.01); *A63B 2220/17* (2013.01); *A63B 2220/803* (2013.01)

(58) Field of Classification Search
CPC . G01P 13/00; A63B 24/0062; A63B 2220/17; A63B 2220/803; G06V 10/98;
(Continued)

(56) References Cited

U.S. PATENT DOCUMENTS

| 2014/0378872 A1* | 12/2014 | Hong ..................... A61B 5/112 600/595 |
| 2016/0066844 A1* | 3/2016 | Venkatraman ......... A61B 5/318 600/509 |

(Continued)

FOREIGN PATENT DOCUMENTS

| CN | 109870172 A | 6/2019 | |
| EP | 1994883 A1 * | 11/2008 | ........... A61B 5/1123 |

OTHER PUBLICATIONS

OA letter of the counterpart I W application (appl. No. 108146765) mailed on Nov. 23, 2020. Summary of the OA letter: 1. Claim 8 has an indefinite claim language. 2. Claims 1, 5~6 and 10 are rejected as being unpatentable over the disclosure of the cited reference 1 (CN 109870172A). 3. Claims 2~4 and 7~9 are allowable.

*Primary Examiner* — Francis C Gray
(74) *Attorney, Agent, or Firm* — WPAT, PC

(57) ABSTRACT

The present disclosure discloses a step counting device that includes a motion detection circuit, a storage circuit and a processing circuit. The motion detection circuit detects a body movement to generate a detection signal. The processing circuit executes computer executable commands to execute the steps outlined below. The detection signal is received from the motion detection circuit. Key data points from the detection signal and representing a simplified waveform are approximated and stored in the storage circuit, each corresponding to a turning data point within a predetermined time period of the detection signal. Periodic waveform sections in the simplified waveform are identified, wherein an error value of waveform parameters between each two of the periodic waveform sections is smaller than a predetermined value. A step group count including a left step and a right step corresponding to each of the periodic waveform sections is accumulated.

10 Claims, 3 Drawing Sheets

(58) Field of Classification Search
CPC .... G06V 40/25; A61B 5/112; G06K 9/00536; G01C 22/006
See application file for complete search history.

(56) References Cited

U.S. PATENT DOCUMENTS

2018/0103859 A1* 4/2018 Provenzano ........... A61B 5/681
2020/0353309 A1* 11/2020 Encarnación Martínez et al. ....... A61B 5/22
2021/0169417 A1* 6/2021 Burton ................. A61B 5/4857

* cited by examiner

STEP COUNTING DEVICE AND METHOD

BACKGROUND OF THE INVENTION

1. Field of the Invention

The present disclosure relates to a step counting device and a step counting method.

2. Description of Related Art

Besides basic functions of communication and time query, portable electronic devices are gaining additional functions. Among functions related to health detection, the step counting function for counting those of a human movement is the most common one.

The step counting function performs step counting based on long period detection of user body movement by using sensors. However, a long period and continuous detection can generate a huge amount of data such that a large amount of computation and storage are required in such electronic devices. Further, the current step counting technology may not be able to distinguish the difference of the left step and the right step of a user, in which the condition of one of the left step and the right step being heavier and the other one being lighter occurs a lot. The occurrence of such a condition may result in lower accuracy of step counting.

SUMMARY OF THE INVENTION

In consideration of the problem of the prior art, an object of the present disclosure is to provide a step counting device and a step counting method.

The present disclosure discloses a step counting device that includes a motion detection circuit, a storage circuit and a processing circuit. The motion detection circuit is configured to detect a body movement to generate a detection signal accordingly. The processing circuit is electrically coupled to the motion detection circuit and the storage circuit and configured to retrieve and execute computer executable commands from the storage circuit to execute a step counting method that includes the steps outlined below. The detection signal is received from the motion detection circuit. A plurality of key data points from the detection signal is approximated and the key data points representing a simplified waveform are stored in the storage circuit, each of the key data points corresponding to a turning data point within a predetermined time period of the detection signal. A plurality of periodic waveform sections are identified in the simplified waveform, wherein an error value of a plurality of waveform parameters between each two of the periodic waveform sections is smaller than a predetermined value. For each of the periodic waveform sections, a step group count comprising a left step and a right step is accumulated.

The present disclosure also discloses a step counting method used in a step counting device that includes the steps outlined below. A body movement is detected to generate a detection signal accordingly by a motion detection circuit. The detection signal is received from the motion detection circuit by a processing circuit. A plurality of key data points from the detection signal is approximated and the key data points representing a simplified waveform are stored in the storage circuit by a processing circuit, each of the key data points corresponding to a turning data point within a predetermined time period of the detection signal. A plurality of periodic waveform sections are identified in the simplified waveform by the processing circuit, wherein an error value of a plurality of waveform parameters between each two of the periodic waveform sections is smaller than a predetermined value. For each of the periodic waveform sections, a step group count comprising a left step and a right step is accumulated by the processing circuit.

These and other objectives of the present disclosure will no doubt become obvious to those of ordinary skill in the art after reading the following detailed description of the preferred embodiments that are illustrated in the various figures and drawings.

DETAILED DESCRIPTION OF THE PREFERRED EMBODIMENTS

An aspect of the present invention is to provide a step counting device and a step counting method to efficiently decrease the storage amount and computation amount required to perform step counting and increase the accuracy of step counting.

Figure 1:
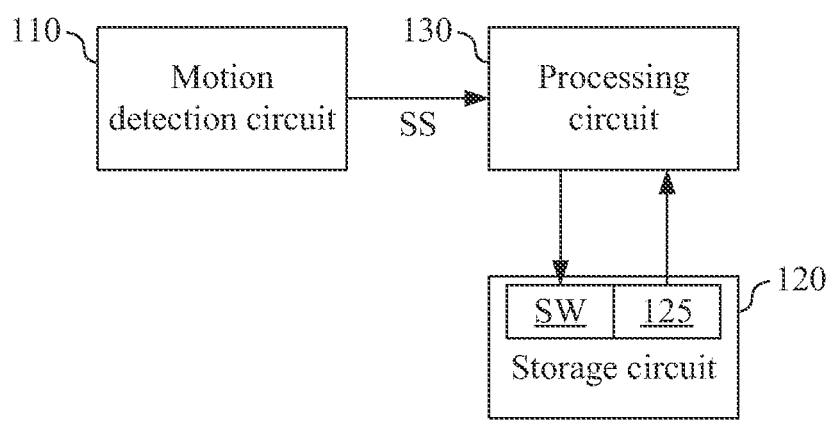
FIG. 1 illustrates a block diagram of a step counting device according to an embodiment of the present invention.

Reference is now made to FIG. 1. FIG. 1 illustrates a block diagram of a step counting device 100 according to an embodiment of the present invention. The step counting device 100 includes a motion detection circuit 110, a storage circuit 120 and a processing circuit 130.

The motion detection circuit 110 can be implemented by such as, but not limited to an acceleration sensor (accelerometer), an angular velocity sensor (gyroscope), a magnetic sensor (magnetometer) or a combination thereof. The motion detection circuit 110 is configured to detect a body movement of a human to generate a detection signal SS accordingly. For example, the motion detection circuit 110 can be disposed in a portable electronic device, e.g. a smartphone or a smart watch, and be put on a user such that a multiple-axis detection of gravity or magnetic force is performed when the user walks and the detection signal SS is generated accordingly.

The storage circuit 120 can be any storage device configured to store data, e.g. random access memory (RAM), read only memory (ROM) or hard drive. It is appreciated that in different embodiments, the storage circuit 120 may include only one of the memory devices mentioned above or may include a multiple of the memory devices mentioned above to store different types of data. In an embodiment, the storage circuit 120 is configured to store computer executable commands 125.

The processing circuit 130 is electrically coupled to the motion detection circuit 110 and the storage circuit 120 and is configured to retrieve and execute the computer executable commands 125 from the storage circuit 120. The computer executable commands 125 include such as, but not limited to firmware, driver and related commands of the hardware modules of the motion detection circuit 110 and the storage circuit 120 to access the signal or data of the motion detection circuit 110 and the storage circuit 120 to perform computation to execute the function of the step counting device 100 to accomplish the object of counting steps of a user.

The operation of the step counting device 100 is described in detail in the following paragraphs.

Firstly, the processing circuit 130 receives a detection signal SS from the motion detection circuit 110. In an embodiment, after receiving the detection signal SS, the processing circuit 130 performs data processing such as, but not limited to smoothing, coordinate conversion based on an axis of the motion detection circuit 110 or a combination thereof on the detection signal SS.

Further, the processing circuit 130 approximates a plurality of key data points from the detection signal SS and stores the key data points representing a simplified waveform SW, in the storage circuit 120. Each of the key data points corresponds to a turning data point within a predetermined time period of the detection signal SS.

Figure 2:
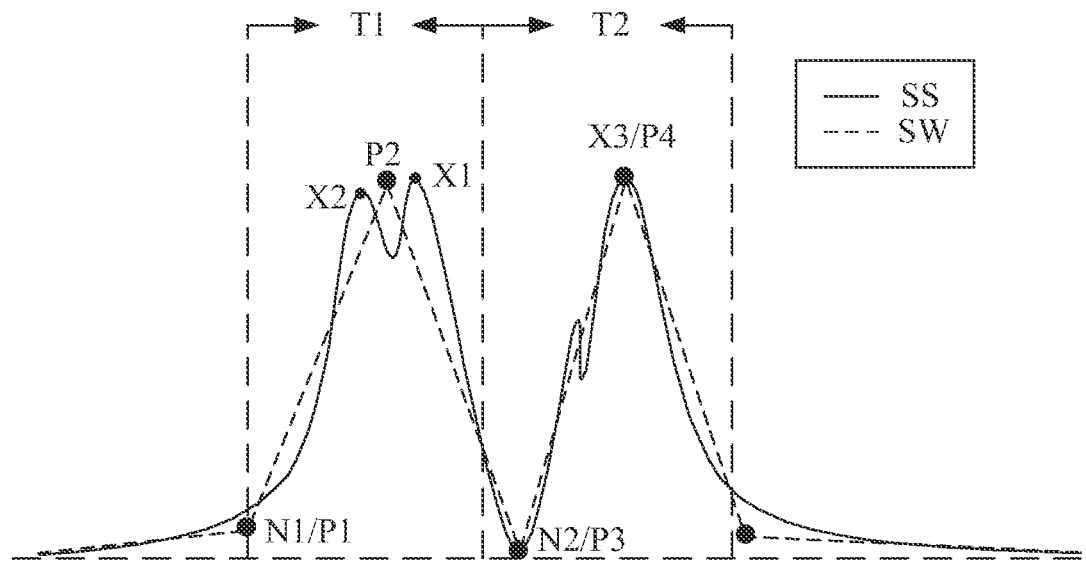
FIG. 2 illustrates a diagram of the detection signal, the key data points retrieved from the detection signal and the simplified waveform formed by the key data points according to an embodiment of the present invention.

Reference is now made to FIG. 2. FIG. 2 is a diagram of the detection signal SS, the key data points P1-P4 retrieved from the detection signal SS and the simplified waveform SW formed by the key data points P1-P4 according to an embodiment of the present invention.

In an embodiment, the processing circuit 130 determines a signal difference value between a highest signal value and a lowest signal value in the predetermined time period. For example, the predetermined time period is 1 second. The processing circuit 130 determines the signal difference value between the highest signal value and the lowest signal value of the detection signal SS in every 1 second.

Take the detection signal SS illustrated in FIG. 2 as an example, in the predetermined time period T1, the processing circuit 130 determines that the highest signal value and the lowest signal value of the detection signal SS are respectively located at a point X1 and a point N1. When the processing circuit 130 determines that the signal difference value between the highest signal value and the lowest signal value is larger than the predetermined value, the points X1 and N1 corresponding to the highest signal value and the lowest signal value are set as key data points.

In an embodiment, the processing circuit 130 can take the condition that whether a local high point and a local low point that have a signal value and a location both close to those of either the highest signal value or the lowest signal value exist into consideration during the determination of the key data points.

When neither a local high point nor a local low point that has the signal value and the location both close to those of either the highest signal value or the lowest signal value exists, the processing circuit 130 directly sets the points X1 and N1 corresponding to the highest signal value and the lowest signal value as the key data points.

Take the detection signal SS illustrated in FIG. 2 as an example, no local low point that has the signal value and the location close to those of the point N1 corresponding to the lowest signal value. As a result, the processing circuit 130 directly sets the point N1 as the key data point P1.

On the other hand, when either a local high point or a local low point that have the signal value and the location both close to those of either the highest signal value or the lowest signal value exists, e.g. a point having a signal value that has a difference from either the highest signal value or the lowest signal value smaller than a predetermined value and having a location that has a distance difference from either the location of the point X1 or the point N1 smaller than a predetermined value, the processing circuit 130 set the key data points simultaneously according to the points X1, N1 and the corresponding local high point and local low points.

Take the detection signal SS illustrated in FIG. 2 as an example, a local high point X2 that has a signal value and a location both close to those of the point X2 corresponding to the highest signal value exists. As a result, the processing circuit 130 can set a point having the signal value of the point X1 (i.e. the highest signal value) and having the location of a middle point between the point X1 and the local high point X2 as the key data point P2.

The embodiment described above is merely an example. In an embodiment, the processing circuit 130 may directly set the points corresponding to the signal highest value and the signal lowest value as the key data points.

Similarly, for the predetermined time period T2, the processing circuit 130 can also determine that the signal difference value between a highest signal value of the point X3 and a lowest signal value of the point N2 in the predetermined time period is larger than a predetermined value at first, and subsequently sets the point X3 and the point N2 respectively corresponding to the highest signal value and the lowest signal value as the key data points.

Since no either local high point or local low point that have the signal values and locations both close to either the highest signal value of the point X3 or the lowest signal value of the point N2 exist, the processing circuit 130 directly sets the point N2 and the point X3 as the key data points P3 and P4.

The processing circuit 130 connects the key data points P1-P4 to form a simplified waveform SW and stores the simplified waveform SW to the storage circuit 120. In other embodiments, the processing circuit 130 may simply store in the storage circuit 120 the key data points P1-P4 representing the simplified waveform SW. By using such a method, the processing circuit 130 can preserve the trend of the detection signal SS while removing the information of the local high point and the local low point of the detection signal SS to decrease the storage amount of the storage circuit 120 and the subsequent amount of computation needed for determining the steps.

Subsequently, the processing circuit 130 identifies a plurality of periodic waveform sections in the simplified waveform SW.

Figure 3:
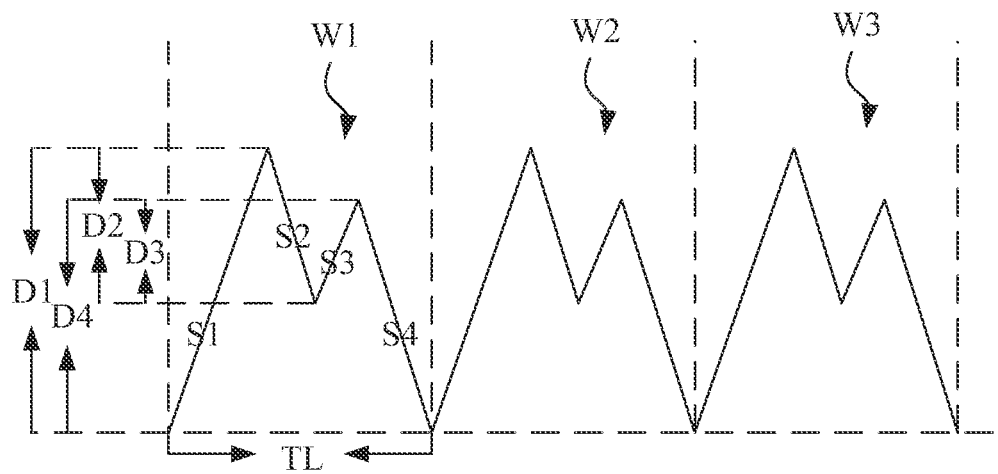
FIG. 3 is a diagram of the simplified waveform according to an embodiment of the present invention.

Reference is now made to FIG. 3. FIG. 3 is a diagram of the simplified waveform SW according to an embodiment of the present invention.

The processing circuit 130 first determines that a plurality waveform sections W1-W3 exist in the simplified waveform SW. Subsequently, the processing circuit 130 determines whether an error value of a plurality of waveform parameters between each two of the waveform sections W1-W3 is smaller than a predetermined value. In an embodiment, take the waveform section W1 as an example, the waveform parameters include such as, but not limited to a waveform time length TL, differences between a peak and a valley D1-D4, waveform slops S1-S4 or a combination thereof. When the error value of the waveform parameters is smaller than the predetermined value, the waveform sections W1-W3 are the periodic waveform sections.

It can be appreciated that in FIG. 3, only three waveform sections W1-W3 are exemplarily illustrated. In other embodiments, the number of the waveform sections included in the simplified waveform SW can be any number that is one or larger than one.

In an embodiment, after identifying the periodic waveform sections, the processing circuit 130 determines that whether a number of the periodic waveform sections included in the simplified waveform SW is smaller than a predetermined value within a detection time.

When the number of the periodic waveform sections included in the simplified waveform SW is not smaller than the predetermined value within the detection time, the processing circuit 130 directly accumulates each of the periodic waveform sections W1-W3 as a step group count that includes a left step and a right step. In practical implementation, one of the left step and the right step of the user is heavier and the other one is lighter such that different shapes of the waveforms corresponding to the left step and the right step that are not periodic and not regular are generated. However, the waveforms of a plurality of step groups, in which each of the step groups includes a left step and a right step, are still periodic and regular. As a result, the processing circuit 130 can determine a complete step group count by using the periodic waveform sections each having a larger interval than that of a single step and having identical waveform parameters and can accumulate each one of step group count as two steps.

When the number of the periodic waveform sections included in the simplified waveform SW is smaller than the predetermined value within the detection time, the processing circuit 130 stores the periodic waveform sections to the storage circuit 120. Further, the processing circuit 130 determines whether the error value of the waveform parameters between the periodic waveform sections and a plurality of previous periodic waveform sections and a plurality of following periodic waveform sections is smaller than the predetermined value. Similarly, the waveform parameters include such as, but not limited to a waveform time length, differences between a peak and a valley, waveform slops or a combination thereof.

When the error value of the waveform parameters between the periodic waveform sections that has a fewer number of occurrence within a short time period and the previous periodic waveform sections and the following periodic waveform sections is smaller than the predetermined value, the processing circuit 130 accumulates each of the periodic waveform sections as a step group count that includes a left step and a right step. On the contrary, when the error value is not smaller than the predetermined value, the processing circuit 130 abandons these periodic waveform sections without accumulating these periodic waveform sections as the step group count.

When the user performs indoor activities, periodic waveform sections within a short time period may occur during a walking activity within a small range or a turnover activity of the body. By using the comparison of the current data, the previous data and the following data, the processing circuit 130 can filter out the activity that is not a normal walking behavior.

As a result, the step counting device can retrieve the key data points of the detection signal to generate the simplified waveform and further determine the periodic waveform sections in the simplified waveform to accumulate the step group count including the left step and the right step. Not only the storage amount and the computation amount of the step counting is decreased, but also the misjudgment caused by the unevenness of the left step and the right step can be avoided. The accuracy of step counting can thus be increased.

Figure 4:
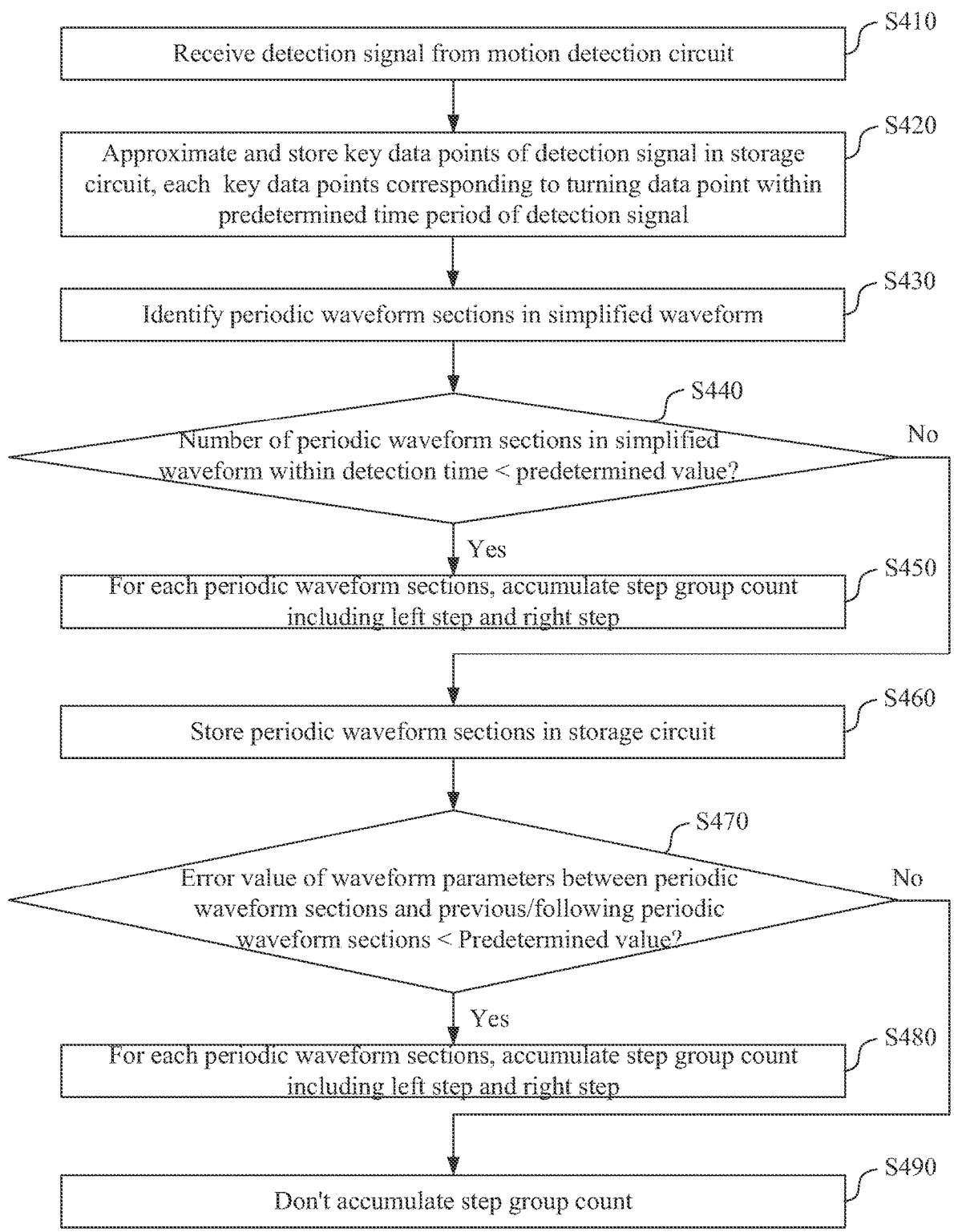
FIG. 4 is a flow chart of a step counting method according to an embodiment of the present invention.

Reference is now made to FIG. 4. FIG. 4 is a flow chart of a step counting method 400 according to an embodiment of the present invention.

Besides the apparatus described above, the present invention further provides the step counting method 400 that can be used in such as, but not limited to the step counting device 100 in FIG. 1. As illustrated in FIG. 4, an embodiment of the step counting method 400 includes the following steps.

In step S410, the detection signal SS is received from the motion detection circuit 110 by the processing circuit 130.

In step S420, the key data points (e.g. the key data points P1-P4 illustrated in FIG. 2) from the detection signal SS are approximated and the key data points representing the simplified waveform SW are stored in the storage circuit 120 by the processing circuit 130. Each of the key data points corresponding to a turning data point within a predetermined time period of the detection signal SS.

In step S430, the periodic waveform sections (e.g. the waveform sections W1-W3 illustrated in FIG. 3) are identified in the simplified waveform SW by the processing circuit 130. An error value of a plurality of waveform parameters between each two of the periodic waveform sections is smaller than a predetermined value.

In step S440, the processing circuit 130 determines that whether a number of the periodic waveform sections included in the simplified waveform SW is smaller than a predetermined value within a detection time.

In step S450, when the number of the periodic waveform sections included in the simplified waveform SW is not smaller than the predetermined value, for each of the periodic waveform sections, the step group count including a left step and a right step is accumulated by the processing circuit 130.

In step S460, when the number of the periodic waveform sections included in the simplified waveform SW is smaller than the predetermined value, the processing circuit 130 stores the periodic waveform sections to the storage circuit 120.

In step S470, the processing circuit 130 further determines whether the error value of the waveform parameters between the periodic waveform sections and a plurality of previous periodic waveform sections and a plurality of following periodic waveform sections is smaller than the predetermined value.

In step S480, when the error value of the waveform parameters between the periodic waveform sections that has a fewer number of occurrence within a short time period and the previous periodic waveform sections and the following periodic waveform sections is smaller than the predetermined value, the processing circuit 130 accumulates each of the periodic waveform sections as a step group count that includes a left step and a right step.

In step S490, when the error value is not smaller than the predetermined value, the processing circuit 130 does not accumulate these periodic waveform sections as the step group count.

It is appreciated that the embodiments described above are merely an example. In other embodiments, it should be appreciated that many modifications and changes may be made by those of ordinary skill in the art without departing from the spirit of the invention.

In summary, the step counting device and the step counting method of the present invention can greatly reduce required the storage amount and computation amount of step counting by generating the simplified waveform to perform step counting according to the periodic waveform sections of the simplified waveform to increase the accuracy of step counting.

The aforementioned descriptions represent merely the preferred embodiments of the present disclosure, without any intention to limit the scope of the present disclosure thereto. Various equivalent changes, alterations, or modifications based on the claims of present disclosure are all consequently viewed as being embraced by the scope of the present disclosure.

What is claimed is:

1. A step counting device, comprising:
a motion detection circuit configured to detect a body movement to generate a detection signal accordingly;
a storage circuit; and
a processing circuit electrically coupled to the motion detection circuit and the storage circuit and configured to retrieve and execute computer executable commands from the storage circuit to execute the steps of:
receiving the detection signal from the motion detection circuit;
approximating a plurality of key data points from the detection signal and storing the key data points representing a simplified waveform in the storage circuit, each of the key data points corresponding to a turning data point within a predetermined time period of the detection signal;
identifying a plurality of periodic waveform sections in the simplified waveform, wherein an error value of a plurality of waveform parameters between each two of the periodic waveform sections is smaller than a predetermined value; and
accumulating, for each of the periodic waveform sections, a step group count comprising a left step and a right step.

2. The step counting device of claim 1, wherein the step counting method comprises:
determining a signal difference value between a highest signal value and a lowest signal value in the predetermined time period to set a plurality points corresponding to the highest signal value and the lowest signal value as the key data points when the signal difference value is larger than a predetermined value.

3. The step counting device of claim 1, wherein the step of identifying the periodic waveform sections in the simplified waveform further comprises:
determining that a plurality of waveform sections exist in the simplified waveform;
determining that whether the error value of the waveform parameters between each two of the periodic waveform sections is smaller than the predetermined value, wherein the waveform parameters comprise a waveform time length, a difference between a peak and a valley, a waveform slop or a combination thereof; and
when the error value of the waveform parameters is smaller than the predetermined value, determining that the waveform sections are the periodic waveform sections.

4. The step counting device of claim 1, wherein the step counting method further comprises:
determining that a number of the periodic waveform sections is smaller than a predetermined value within a detection time;
storing the periodic waveform sections to the storage circuit;
determining whether the error value of the waveform parameters between the periodic waveform sections and a plurality of previous periodic waveform sections and a plurality of following periodic waveform sections is smaller than the predetermined value; and
when the error value is smaller than the predetermined value, for each of the periodic waveform sections, accumulating the step group count comprising the left step and the right step.

5. The step counting device of claim 1, wherein the step counting method further comprises:
performing data processing comprising smoothing, coordinate conversion or a combination thereof on the detection signal.

6. A method comprising:
detecting a body movement to generate a detection signal accordingly by a motion detection circuit;
receiving the detection signal from the motion detection circuit by a processing circuit;
approximating a plurality of key data points from the detection signal and storing the key data points representing a simplified waveform in a storage circuit by the processing circuit, each of the key data points corresponding to a turning data point within a predetermined time period of the detection signal;
identifying a plurality of periodic waveform sections in the simplified waveform by the processing circuit, wherein an error value of a plurality of waveform parameters between each two of the periodic waveform sections is smaller than a predetermined value; and
accumulating for each of the periodic waveform sections a step group count comprising a left step and a right step by the processing circuit.

7. The method of claim 6, further comprising:
determining a signal difference value between a highest signal value and a lowest signal value in the predetermined time period to set a plurality points corresponding to the highest signal value and the lowest signal value as the key data points when the signal difference value is larger than a predetermined value.

8. The method of claim 6, wherein the step of identifying the periodic waveform sections in the simplified waveform further comprises:
determining that a plurality of waveform sections exist in the simplified waveform;
determining that whether the error value of the waveform parameters between each two of the periodic waveform sections is smaller than the predetermined value, wherein the waveform parameters comprise a waveform time length, a difference between a peak and a valley, a waveform slop or a combination thereof; and
when the error value of the waveform parameters is smaller than the predetermined value, determining that the waveform sections are the periodic waveform sections.

9. The method of claim 6, further comprising:
determining that a number of the periodic waveform sections is smaller than a predetermined value within a detection time;
storing the periodic waveform sections to the storage circuit;
determining whether the error value of the waveform parameters between the periodic waveform sections and a plurality of previous periodic waveform sections and a plurality of following periodic waveform sections is smaller than the predetermined value; and
when the error value is smaller than the predetermined value, for each of the periodic waveform sections, accumulating the step group count comprising the left step and the right step.

10. The method of claim 6, further comprising:
performing data processing comprising smoothing, coordinate conversion or a combination thereof on the detection signal.

* * * * *